(12) United States Patent
Quinn et al.

(10) Patent No.: US 11,582,989 B2
(45) Date of Patent: *Feb. 21, 2023

(54) STRESS MANAGEMENT IN LIVESTOCK

(71) Applicant: Charles Sturt University, Wagga Wagga (AU)

(72) Inventors: Jane Quinn, Wagga Wagga (AU); Scott Edwards, Wagga Wagga (AU); Martin Combs, Wagga Wagga (AU)

(73) Assignee: CHARLES STURT UNIVERSITY, Wagga Wagga (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/129,316

(22) Filed: Dec. 21, 2020

(65) Prior Publication Data
US 2021/0112828 A1    Apr. 22, 2021

Related U.S. Application Data

(63) Continuation of application No. 16/377,862, filed on Apr. 8, 2019, now Pat. No. 10,897,917, which is a continuation of application No. 15/038,261, filed as application No. PCT/AU2014/050362 on Nov. 20, 2014, now Pat. No. 10,271,566.

(30) Foreign Application Priority Data

Nov. 20, 2013   (AU) ................................ 2013904516

(51) Int. Cl.
| | |
|---|---|
| A23K 20/24 | (2016.01) |
| A23K 20/20 | (2016.01) |
| A23K 20/22 | (2016.01) |
| A23K 50/10 | (2016.01) |
| A61K 33/00 | (2006.01) |
| A61K 9/00 | (2006.01) |

(52) U.S. Cl.
CPC .............. *A23K 20/24* (2016.05); *A23K 20/20* (2016.05); *A23K 20/22* (2016.05); *A23K 50/10* (2016.05); *A61K 9/0095* (2013.01); *A61K 33/00* (2013.01)

(58) Field of Classification Search
CPC ................................ A23K 50/00; A23K 50/10
See application file for complete search history.

(56) References Cited

U.S. PATENT DOCUMENTS

| | | |
|---|---|---|
| 3,017,272 A | 1/1962 | Van Dijck et al. |
| 4,192,865 A | 3/1980 | Helbig |
| 5,980,928 A | 11/1999 | Terry |
| 9,913,858 B2 | 3/2018 | Quinn et al. |
| 10,271,566 B2 | 4/2019 | Quinn et al. |
| 2001/0031276 A1* | 10/2001 | Shelford ............... A23K 20/189 424/442 |
| 2005/0277624 A1 | 12/2005 | Cook |
| 2016/0296553 A1 | 10/2016 | Quinn et al. |
| 2016/0296554 A1 | 10/2016 | Quinn et al. |

FOREIGN PATENT DOCUMENTS

| | | |
|---|---|---|
| HU | 186119 B | 6/1985 |
| SU | 1246448 A1 | 2/1987 |
| UA | 22020 U | 4/2007 |
| WO | 2002085132 A1 | 10/2002 |
| WO | 2015074114 A1 | 5/2015 |
| WO | 2015074115 A1 | 5/2015 |

OTHER PUBLICATIONS

Rossmeisl et al. AVMA, 2009, 234(11), abstract, 1 pgs.*
Fielding et al., Pharmacokinetics and Clinical Utility of Sodium Bromide (NaBr) as an Estimator of Extracellular Fluid Volume in Horse, (2003), Journal of Veterinary Internal Medicine, 17:213-217.
Genicot, B. et al.; "Efficiency of a sedative on the behaviour and the performances of Belgian white and blue double-muscled cattle during fattening"; Paul Parey Scientific Publishers, Berlin and Hamburg; J. Vet. Med. A 38, 668-675 1991; Nov. 6, 1990.
Knight et al., Intoxication of Cattle with Sodium Bromide-Contaminated Feed, (1997), American Journal of Veterinary Research, 38:407-409.
Monastyrev, A. M.; "Use of tranquilizers in transporting of cattle"; Donskoi S-kh Inst.; Soversh. Tekhnol. Ved. Myasn. Skotovod. Prom. Osn. (1986). 101-4: published in 1986.
Raidal et al., Pharmacokinetics of potassium bromide in adult horses, (2008), Australian Veterinary Journal, vol. 86, No. 5; 187-193.
Thodesen, Jorn et al.; "Feed intake, growth and feed utilization of offspring from wild and selected Atlantic salmon (*Salmo salar*)"; Akvaforsk (Institute of Aquaculture Research); Aquaculture 180 (1999) 23 7-246; Apr. 26, 1999; pp. 237-246.
Trepanier et al., Pharmacokinetic properties of bromide in dogs after the intravenous and oral administration of single doses., (1995), Research in Veterinary Science, 58:248-251.
Wang, J.; "Eight Measures to Reduce the Stress Responses of Cattle during Transportation"; Agriculture of Henan, 5: J3; published 2003; pp. 1-2.
Zhang, Y.; "Sedating Hogs to Reduce Weight Loss during Transportation"; Hubei Animal Husbandry Veterinarian, 1:34; published 1981; pp. 1-2.
PCT; PCT App. No. PCT/AU2014/050363; Search report and opinion dated Dec. 17, 2014.
PCT; PCT App. No. PCT/AU2014/050362; Search report and opinion dated Dec. 16, 2014.
EPO; App. No. 14863191.4; European Extended Search Report for European Application dated Apr. 11, 2017.
EPO; App. No. 14863191.4; European Office Action for European Application dated Dec. 3, 2019.
EPO; App. No. 14863191.4; European Office Action for European Application dated Feb. 22, 2019.
EPO; App. No. 14863191.4; European Office Action for European Application dated Jul. 26, 2018.

* cited by examiner

*Primary Examiner* — Kyle A Purdy
(74) *Attorney, Agent, or Firm* — Fitch, Even, Tabin & Flannery LLP

(57) ABSTRACT

A method for minimising or preventing the induction of stress-related or stress-induced inappetance or inanition in an animal selected for a marketing or management practice.

17 Claims, 9 Drawing Sheets

STRESS MANAGEMENT IN LIVESTOCK

CROSS-REFERENCE TO RELATED APPLICATIONS

This application is a continuation of U.S. application Ser. No. 16/377,862, filed Apr. 8, 2019, which is a continuation of U.S. application Ser. No. 15/038,261, having a 371(c) date of May 20, 2016, which is a national stage entry of PCT Application Number PCT/AU2014/050362, filed Nov. 20, 2014, which claims priority to Australian Application Number 2013904516, filed Nov. 20, 2013, which are all incorporated by reference in their entirety herein.

FIELD OF THE INVENTION

This invention relates to prevention of stress in livestock, especially ruminant animals.

BACKGROUND OF THE INVENTION

Many of the management practices to which livestock and ruminant animals are subjected can be potent physiological and psychological stressors that impact on the performance of the animal. Common on-farm husbandry practices including tail docking, marking, mulesing, castration and dehorning are of particular concern, as are a number of other management practices including weaning, transport, feedlot integration and other integration practices leading to mixing of unfamiliar animals, release of animals into an unfamiliar environment or into confined conditions, or presentation with unfamiliar feeds.

One manifestation of these stressors is inanition, otherwise known as exhaustion resulting from lack of nourishment. In particular, ruminant animals, which are highly susceptible to development of stress-induced conditions such as anxiety, tend to reduce their nutrient intake (resulting in inappetance), and leading to inanition and reduced growth performance and productivity. This is particularly seen in transport of live animals, especially in live export, and in the introduction of animals into feedlots for finishing.

There have been a number of approaches to addressing the problem. Many of these have generally focussed on treatment of animals that have been exposed to stressors, and with no particular focus on preparing an animal prior to implementation of a management practice so that, as prepared, the animal is then less susceptible to the stressors arising from, or associated with, the relevant practice.

There remains a need to minimise stress-induced inanition in livestock production (for example by minimising, or reducing the likelihood of, inappetance), and in particular in the management and marketing of ruminant animals.

There is a particular need to minimise stress-induced inanition in animals selected for husbandry procedures, including mulesing, tail docking, marking and castration, as well as dehorning in cattle and deer, and any act of veterinary science either separate to, or in conjunction with, husbandry procedures.

There is also a need to minimise stress-induced inanition in animals selected for transport, including transport for other than slaughter purposes, and including live export.

There is also a need to minimise stress-induced inanition in animals selected for feedlot integration.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The invention seeks to address one or more of the above mentioned problems or needs, and in one embodiment provides for the treatment or preparation of an animal. The preparation of the animal is implemented prior to subjecting the animal to a marketing or management practice. This prior implementation minimises or prevents the induction of stress or anxiety-related inanition in the animal during, or at completion of, the practice. The preparation involves the administration of a formulation including bromide. The bromide is provided in an amount effective for preventing the animal from reducing feed intake, or more generally, from exhibiting reduced growth or productivity from lack of nourishment.

In one embodiment, the invention provides a method for the preparation of an animal prior to subjecting the animal to a marketing or management practice, thereby minimising or preventing the induction of stress or anxiety-related inanition in the animal during, or at completion of, the practice, the method including the step of administering a formulation including bromide to an animal selected for the marketing or management practice in an amount effective for preventing the animal from reducing feed intake.

In one embodiment, the invention provides a method for preparation of an animal for a marketing or management practice, thereby minimising or preventing the induction of stress or anxiety-related inanition in the animal during, or at completion of, the practice, the method including the step of administering a formulation including bromide to an animal selected for the marketing or management practice in an amount effective for preventing the animal from reducing feed intake.

In certain embodiments, the invention provides a method for preparing an animal for a husbandry procedure so as to minimise the likelihood of the animal developing stress or anxiety-related inanition subsequent to the procedure, the method including:

providing bromide to an animal that has been selected for a husbandry procedure in an amount sufficient for minimising the development of stress or anxiety-related inanition in the animal;

thereby preparing the animal for the husbandry procedure.

In another embodiment, the invention provides a method for preparing an animal for transport so as to minimise the likelihood of the animal developing stress or anxiety-related inanition during or subsequent to transport, the method including:

providing bromide to an animal that has been selected for transport in an amount sufficient for minimising the development of stress or anxiety-related inanition in the animal;

thereby preparing the animal for transport.

In a further embodiment, the invention provides a method for preparing an animal for feedlot integration so as to minimise the likelihood of the animal developing stress or anxiety-related inanition subsequent to feedlot integration, the method including:

providing bromide to an animal that has been selected for feedlot integration in an amount sufficient for minimising the development of stress or anxiety-related inanition in the animal;

thereby preparing the animal for feedlot integration.

In the above described methods, in one embodiment, the animal to which the invention is applied does not have stress or anxiety-related inanition or inappetance at the time of administration of the formulation. For example, the feed intake or growth performance of the animal up to the time of administration of the formulation is generally considered to have been normal in the context of the relevant age, physiology and environment pertaining to the animal.

In further embodiments there are provided compositions and kits suitable for use in the above described methods.

In one embodiment, the animal is a ruminant (e.g. ovine or bovine).

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
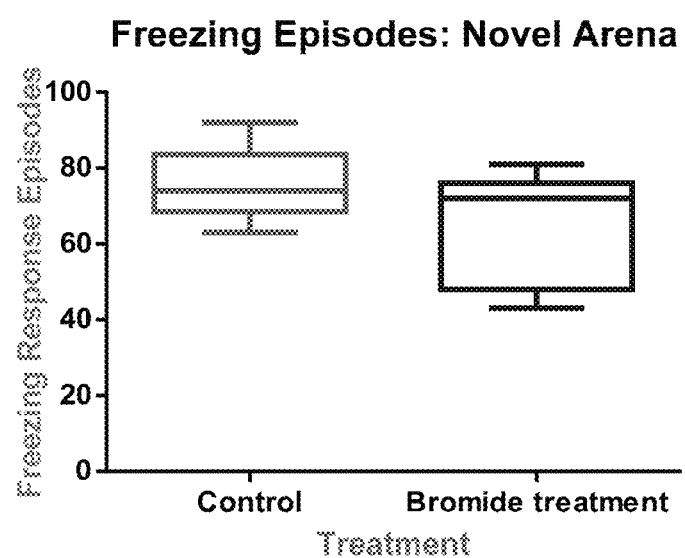
FIG. 1. Freezing response episodes in C57/B16, 4 month old male mice given oral potassium bromide 250 mg/L (n=9) or normal drinking water (n=5) for 7 days prior novel arena testing.

As described herein, the inventors have found that bromide may be used prophylactically to prevent an animal from developing stress-induced or stress-related inanition or related eating disorders arising from or associated with a reduced nutrient intake (inappetance being an example) after the animal has been subjected to a management or marketing practice, such as a husbandry practice, transport or feedlot integration practice, other acts of veterinary science, or a combination of the above.

While not wanting to be bound by hypothesis, the inventors believe that the utility of bromide in the invention arises from the interaction of bromide with the nervous system which desensitises the animal to stress insults arising from the relevant procedure, or which otherwise decreases the animal's perception of these stress insults.

In accordance with the invention, in one embodiment there is provided a method for the preparation of an animal prior to subjecting the animal to a marketing or management practice, thereby minimising or preventing the induction of stress or anxiety-related inanition in the animal during, or at completion of, the practice. The method includes the step of administering a formulation including bromide to an animal selected for the marketing or management practice in an amount effective for preventing the animal from reducing feed intake, or from exhibiting reduced growth or productivity from lack of nourishment.

According to the invention, the relevant stress is that generally arising from farming practices, including management and marketing practices that the animal is routinely subjected to. In some contexts the stress may be referred to as 'ante mortem' stress which is generally understood to be stress that occurs pre-slaughter, and also more broadly in across the animal production lifecycle. Examples of relevant stress include stress resulting from transport, holding, handling, containment, changes in feed or environment, mixing with unfamiliar animals and other like management practices relevant to livestock animals. Stress arising from transport, feedlot integration and other integration practices leading to mixing of unfamiliar animals, or release of animals into an unfamiliar environment are of particular concern, as is stress arising from husbandry practices such as mulesing, tail docking, dehorning, castration and marking procedures, and any other act of veterinary science.

In one embodiment, the marketing or management practice is a husbandry practice.

In accordance with the invention, there is provided a method for preparing an animal for a husbandry practice so as to minimise the likelihood of the animal developing stress or anxiety-related inanition subsequent to, or during, the practice, the method including:

providing bromide to an animal that has been selected for a husbandry practice in an amount sufficient for minimising the development of stress or anxiety-related inanition in the animal;

thereby preparing the animal for the husbandry practice.

In one embodiment, the husbandry practice is mulesing, marking, castration or dehorning.

In one embodiment, the marketing or management practice is animal transport.

Accordingly, the invention also provides a method for preparing an animal for transport so as to minimise the likelihood of the animal developing stress or anxiety-related inanition during or subsequent to transport, the method including:

providing bromide to an animal that has been selected for transport in an amount sufficient for minimising the development of stress or anxiety-related inanition in the animal;

thereby preparing the animal for transport.

In one embodiment, marketing or management practice is introduction of the animal into a feedlot.

Accordingly, the invention also provides a method for preparing an animal for feedlot integration so as to minimise the likelihood of the animal developing stress or anxiety-related inanition subsequent to feedlot integration, the method including:

providing bromide to an animal that has been selected for feedlot integration in an amount sufficient for minimising the development of stress or anxiety-related inanition in the animal;

thereby preparing the animal for feedlot integration.

Typically an animal to which the invention is applied does not have stress or anxiety-related inanition or inappetance at the time of administration of the formulation. For example, the feed intake or growth performance of the animal up to the time of administration of the formulation is generally considered to have been normal in the context of the relevant age, physiology and environment pertaining to the animal.

In one embodiment, the animal does not have a movement disorder such as an abnormal gait, or a disorder arising from grass toxicosis, at the time of administration of the formulation.

As used herein, the term "preparation" or "preparing" refers to the use of the bromide in a prophylactic or preventative sense. That is, preparing an animal for a marketing or management practice involves administering bromide (or a formulation including bromide) to the animal before it is subjected to the marketing or management practice so as to minimise, or reduce, or prevent the stress or anxiety-related inanition that the animal would otherwise experience in the absence of said preparation. Successful preparation of the animal will be achieved when the animal's normal feed intake is not significantly reduced or affected, or where the animal does not become significantly exhausted, disabled, or does not exhibit reduced productivity from lack of nourishment. For example, the animal's growth performance will not be significantly affected (e.g. the animal's weight, reproductive performance and/or milk production will remain around normal levels or increase).

As used herein, the term "animal" refers to domestic ruminant and monogastric animals, including swine, horses, cattle, bison, sheep, deer, moose, elk, caribou and goats, of any age.

In one embodiment, the animal is a ruminant. Preferred ruminants include ovine (i.e. sheep) and bovine (i.e. cattle). In one embodiment, the animal is not an equine. The invention is also not intended to cover humans. Therefore, in one embodiment, the animal is not a human.

As used herein, "bromide" refers to the bromine ion ($Br^-$). It will be understood by a person skilled in the art that bromide will generally be administered to the animal in the form of a salt and/or other compound with a bromine group that readily dissociates in situ and/or in vivo to give bromide. Preferably, the bromide is in the form of a salt, which may contain an alkali metal or alkaline earth metal. For example, the bromide may be in the form of potassium bromide, sodium bromide or magnesium bromide. Potassium bromide and magnesium bromide are particularly useful for oral administration and sodium bromide is useful for intravenous administration. Magnesium bromide has a higher percentage of bromide than both the potassium and sodium salts, and possesses much greater water solubility than both the potassium and sodium salts.

Consequently, magnesium bromide solutions can be made at much higher bromide concentrations than other salts, before saturation is reached. This property of the magnesium salt of bromide impacts on formulation; low volume delivery is practically and economically advantageous.

In one embodiment, bromide is provided in an amount of about 10 to about 750 mg/kg animal weight per dose. For example, the bromide may be provided in an amount of from about 20 to about 600 mg/kg animal weight per dose (e.g. from about 30 to about 500 mg/kg animal weight, from about 50 to about 400 mg/kg animal weight or from about 100 mg/kg to about 300 mg/kg animal weight). In one embodiment, the bromide is provided in an amount of about 300 mg/kg animal weight per dose.

Bromide may be provided in an amount of about 10 mg/kg, about 20 mg/kg, about 50 mg/kg, about 75 mg/kg, about 100 mg/kg, about 120 mg/kg, about 150 mg/kg, about 200 mg/kg, about 250 mg/kg, about 300 mg/kg, about 350 mg/kg, about 400 mg/kg, about 450 mg/kg, about 500 mg/kg, about 550 mg/kg, about 600 mg/kg, about 650 mg/kg, about 700 mg/kg or about 750 mg/kg per dose.

In one embodiment, the bromide (e.g. in a formulation including bromide) is administered in an amount to provide an animal with about 10 to about 500 mg/kg animal weight of bromide. For example, the bromide may be in an amount to provide the animal with from about 20 to about 600 mg/kg animal weight (e.g. from about 30 to about 500 mg/kg animal weight, or from about 50 to about 400 mg/kg animal weight) of bromide. In one embodiment, the bromide is in an amount to provide an animal with about 300 mg/kg animal weight of bromide.

Bromide (e.g. in a formulation including bromide) may be administered in an amount to provide an animal with about 10 mg/kg, about 20 mg/kg, about 50 mg/kg, about 75 mg/kg, about 100 mg/kg, about 120 mg/kg, about 150 mg/kg, about 200 mg/kg, about 250 mg/kg, about 300 mg/kg, about 350 mg/kg, about 400 mg/kg, about 450 mg/kg, about 500 mg/kg, about 550 mg/kg, about 600 mg/kg, about 650 mg/kg, about 700 mg/kg or about 750 mg/kg animal weight of bromide.

It will be understood that the specific dose level of bromide for any particular animal may depend upon a variety of factors including the activity of the specific bromide employed, the age, body weight, general health, sex and/or diet of the animal, time of administration, route of administration, and rate of excretion, drug or supplement combination (i.e. other drugs or supplements being used concomitantly with the bromide), and the severity of the stress being exhibited, if being used as a treatment.

In one embodiment, bromide is the only active in the formulation. In one embodiment, bromide is the only active provided to the animal. Therefore, in one embodiment, the method of the present invention does not include providing therapeutic or nutritive agents, other than bromide, to the animal. Examples of such agents include electrolytes (e.g. sodium, potassium, magnesium, manganese, chromium, and calcium, and chloride, oxide, carbonate and aspartate salts thereof), amino acids (or salts thereof), and sources of energy (e.g. sugar).

Typically the formulation is provided once daily for a period of one day to no more than about four weeks prior to the time the animal is subjected to the marketing or management practice. In one embodiment, the formulation is provided once prior to subjecting the animal to a marketing or management practice. The formulation may be provided immediately prior to subjecting the animal to a marketing or management practice, or may be provided from one to 24 hours prior to subjecting the animal to a marketing or management practice.

In another embodiment, bromide is not given on or after completion of the marketing or management practice.

A dose of a bromide-containing formulation of the invention may be delivered at once, for example, as a bolus, or over the course of several hours.

Theoretically there is no maximum limit for the dosage provided that the bromide does not accrue in the animal to a point whereby it diminishes the quality of the animal or products therefrom.

The bromide may be provided in the form of a formulation adapted for delivery by an animal handler, or for consumption by the animal. Examples are described further herein.

In one embodiment, the invention provides a formulation for use in preventing the induction of stress or anxiety-related inanition in an animal during, or at completion of, a marketing or management practice on an animal selected for the practice, the formulation including bromide in an amount for preventing the induction of stress or anxiety-related inanition in the animal, the formulation for administration to the animal, prior to subjecting the animal to the practice, in any of the embodiments described in the specification.

In one embodiment, the method includes a further step of administering a formulation including bromide to the animal at completion of the marketing or management practice, or thereafter. It will be understood that in this embodiment the animal selected for the relevant procedure first receives the bromide formulation before the relevant procedure. At the completion of the procedure, the animal may then receive further bromide for a pre-determined period. In this embodiment, typically the formulation is provided daily for a period of one day to no more than four weeks from completion of the marketing or management practice.

The formulation may be provided in a range of forms depending on the route of administration required. For example, the formulation may be adapted for injection intravenously, intramuscularly or subcutaneously, for oral, topical, ocular or nasal delivery, or for anal or vaginal delivery. Preferably the formulation is administered orally or intravenously. Accordingly, preferably, the formulation is provided in the form of a drench, or in the form of an injectable composition adapted for intravenous injection of the formulation.

In one embodiment, the formulation includes, in addition to the bromide, one or more pharmaceutically-acceptable excipients, such as binders, disintegrants, dispersants, lubricants, colours, flavours, coatings, glidants, sorbents, absorption-enhancing agents, emulsifiers, surfactants, buffers, bulking agents, tonicity-adjusting agents, preservatives, wetting agents, solvents, and sweeteners. Suitable examples of excipients to include in formulations for use in the invention are well-known to a person skilled in the art.

Suitable formulations for use in the present invention include drenches, gels, pastes, tablet/bolus formulations, gelatin capsules, injectable formulations, or intraruminal devices for slow release of the active.

In one embodiment the invention provides a drench including bromide, wherein the drench includes bromide in an amount to provide an animal with about 20 to about 500 mg bromide/kg animal weight of bromide. In one embodiment, the drench includes bromide in an amount to provide an animal with about 20 to about 400 mg/kg animal weight (e.g. from about 30 to about 300 mg/kg animal weight, or from about 50 to about 400 mg/kg animal weight) of bromide. In one embodiment, the drench includes bromide in an amount to provide an animal with about 300 mg/kg animal weight of bromide.

In one embodiment, the drench includes bromide in an amount to provide an animal with about 20 mg/kg, about 50 mg/kg, about 75 mg/kg, about 100 mg/kg, about 120 mg/kg, about 150 mg/kg, about 200 mg/kg, about 250 mg/kg, about 300 mg/kg, about 350 mg/kg, about 400 mg/kg, about 450 mg/kg or about 500 mg/kg animal weight of bromide.

Preferred drenches are those adapted for use in a ruminant animal, particularly sheep (ovine) or cattle (bovine). Preferably the concentration of bromide in the drench is from about 5 to about 70% w/v (liquid or paste formulation) and about 5 to about 70% w/w (powder or solid formulation). In one embodiment, the concentration of bromide in the drench is from about 10 to about 60%, from about 20 to about 50%, or from about 30 to about 40% w/v or w/w. In one embodiment, the concentration of bromide in the drench is about 5, about 10, about 20, about 30, about 40, about 50, about 60 or about 70% w/v or w/w.

In one embodiment, the only active in the drench is bromide.

In one embodiment, the drench is adapted for use in a monogastric animal.

In another embodiment the invention provides an injectable formulation including bromide, wherein the formulation includes bromide in an amount to provide an animal with about 10 to about 500 mg/kg animal weight of bromide. In one embodiment, the injectable formulation includes bromide in an amount to provide an animal with about 20 to about 400 mg/kg animal weight (e.g. from about 30 to about 300 mg/kg animal weight, or from about 50 to about 400 mg/kg animal weight) of bromide. In one embodiment, the injectable formulation includes bromide in an amount to provide an animal with about 300 mg/kg animal weight of bromide.

In one embodiment, the injectable formulation includes bromide in an amount to provide an animal with about 10 mg/kg, about 20 mg/kg, about 50 mg/kg, about 75 mg/kg, about 100 mg/kg, about 120 mg/kg, about 150 mg/kg, about 200 mg/kg, about 250 mg/kg, about 300 mg/kg, about 350 mg/kg, about 400 mg/kg, about 450 mg/kg or about 500 mg/kg animal weight of bromide.

Preferably the formulation is adapted for application to a ruminant animal, such as sheep (ovine) or cattle (bovine). Preferably the concentration of bromide is from 5 to 70% to (w/v). In one embodiment, the concentration of bromide in the formulation is from about 10 to about 60%, from about 20 to about 50%, or from about 30 to about 40% w/v. In one embodiment, the concentration of bromide in the formulation is about 5, about 10, about 20, about 30, about 40, about 50, about 60 or about 70% w/v.

In one embodiment, the only active in the injectable formulation is bromide.

The drench or injectable formulation may be provided in the form of a kit including written instructions enabling use of the kit in a method described above. In one embodiment, the invention provides a kit including a drench, as described herein, and written instructions enabling use of the kit in a method described herein. In one embodiment, the invention provides a kit including an injectable formulation, as described herein, and written instructions enabling use of the kit in a method described herein.

In one embodiment, the invention also provides use of bromide in the manufacture of a formulation for minimising or preventing the induction of stress or anxiety-related inanition in an animal during, or at completion of, a marketing or management practice, the formulation for administration to the animal selected for marketing or management practice, prior to subjecting the animal to the practice.

In one embodiment, the invention also provides a formulation for use in preventing the induction of stress or anxiety-related inanition in an animal during, or at completion of, a marketing or management practice on an animal selected for the practice, the formulation including bromide in an amount for preventing the induction of stress or anxiety-related inanition in the animal, the formulation for administration to the animal, prior to subjecting the animal to the practice.

In one embodiment, the invention also provides a formulation when used in a method of preventing the induction of stress or anxiety-related inanition in an animal during, or at completion of a marketing or management practice on an animal selected for the practice, the formulation including bromide in an amount for preventing the induction of stress or anxiety-related inanition in the animal, the formulation for administration to the animal, prior to subjecting the animal to the practice.

In one embodiment, the invention also provides a formulation having an active ingredient for use in a method of preventing the stress or anxiety-related inanition in an animal during, or at completion of, a marketing or management practice on an animal selected for the practice, wherein the active ingredient is bromide and wherein the bromide is present in an amount for preventing the induction of stress or anxiety-related inanition in the animal, the formulation for administration to the animal, prior to subjecting the animal to the practice.

In one embodiment, the invention also provides the use of a formulation containing bromide in preventing the induction of stress or anxiety-related inanition in an animal during, or at completion of, a marketing or management practice on an animal selected for the practice, wherein the active ingredient is bromide and wherein the bromide is present in an amount for preventing the induction of stress or anxiety-related inanition in the animal, the formulation for administration to the animal, prior to subjecting the animal to the practice, such as described herein.

In an alternative embodiment, the bromide may be provided in the form of a supplement in liquid (e.g. an aqueous solution) or solid form that is to be consumed by the animal. The bromide may be dissolved in the animal's drinking water for the animal to consume. The bromide may be incorporated into animal feed as a means to administer the bromide to the animal and/or encourage the animal to consume the bromide. Animal feed includes any food that the animal is capable of ingesting and if desired, any additional ingestable materials. For example, it could include grass, plant extracts, vitamins, minerals, feed supplements and other such materials.

In one embodiment, bromide is provided with feed in an amount of between about 0.01 to about 5% w/w dry matter. For example, bromide may be provided in an amount of between about 0.5 and about 4% or about 1 and about 3% w/w dry matter. In one embodiment, the concentration of bromide in feed is about 0.01, about 0.1, about 0.2, about 0.5, about 1, about 2, about 3, about 4 or about 5% w/w dry matter.

The bromide may be administered with another medication (e.g. an antibiotic), a growth promotant or incorporated into a mineral pre-mix. Suitable amounts of bromide in this regard include between about 0.1 and about 60% w/w dry weight. For example, bromide may be provided in an amount of between about 0.5 and about 50%, about 1 and about 40%, about 5 and about 30% or about 10 and about 20% w/w dry weight. In one embodiment, the concentration of bromide is about 0.1, about 0.2, about 0.5, about 1, about 2, about 5, about 10, about 15, about 20, about 25, about 30, about 35, about 45, about 50, about 55 or about 60% w/w dry matter.

It will be evident that, given the variable consumption of solids and liquids by animals, the amount of bromide in a consumable composition as stated above is approximate and may be varied depending on the type of formulation (solid v. liquid), the solubility of the bromide, the body weight of the animal and the average solid and liquid intake of the animal. Supplements may be provided with carriers, or may be formulated into feed with binders. Exemplary carriers include grain or grass by-products, such as oats, barley, wheat, canola, rye, sorgum, millet, corn, legumes and grasses.

Typically, an animal treated by the method of the invention disclosed herein retains a normal feed intake subsequent to the marketing or management practice. It may be possible to further modify that feed intake by providing an appetite stimulant to the animal, prior to, during or after the completion of the marketing or management practice.

In one embodiment, the present invention includes the further step of providing an appetite stimulant to the animal prior to, during, or after the completion of the marketing or management practice.

Example 1—Bromide Decreases Stress-Induced Inanition in Stress Treated Rodents

Monitoring Stress and Anxiety Behaviours in Rodents

A model system was established to induce stress in rodents by repeated behavioural testing using the AnyMaze™ rodent behavioural monitoring system. To determine the effects of bromide on these animals, age, sex and strain matched animals were treated for 7 days with 250 mg/L potassium bromide in drinking water and subjected to mild stressors such as handling and weighing. At the end of 7 days animals were subjected to a number of behavioural tests to assess level of stress. Weight gain was also analysed in the treatment group by recording body weight over the initial 7 day period.

Results: Animals treated with bromide showed a trend towards decreased freezing response episodes (a behavioural stress response) and increased weight gain over the trial period (7 days)

Conclusions and clinical relevance: These data support potassium bromide as an efficacious therapeutic treatment to alleviate stress related behaviours and increase appetite in animals suffering from stress.

Materials and Methods

Determination of a Mild Stress Model in Rodents

C57B16/Ola male mice at 5 weeks of age were purchased from MAS Client Services, Monash University, Melbourne, Australia. Animals were weighed at the start of the test period and daily for the duration of testing. Potassium bromide was administered in drinking water to 5 animals for 7 days at 250 mg/L, 5 control animals received water alone.

Behavioural Testing

Animals were weighed 3 times during the experiment (7 days). To initiate a mildly stressful situation, animals were exposed to novel arena, parallel rod and tremor tests using the mouse AnyMaze™ system (AnyMaze™, Stoelting, U.S.A.).

Novel Arena

Animals were placed in the centre of an open arena which was unfamiliar to them and their rate and range of movement tracked by digital recognition software. Distance, speed and time spent immobile were analysed using the AnyMaze™ software. Results were compared statistically using SPSS™.

Parallel Rod

The parallel rod test analyses changes in rate and range of movement as well as coordination. Briefly, animals are placed into a cage at the bottom of which is an electrified grid. If the animal places a foot below the grid and onto the floor a circuit will be activated and this abnormal footfall registered as an event. AnyMaze™ tracking software also monitors rate of movement and periods of immobility.

Tremor Testing

Animals were placed in a tremor sensor box and a clear lid placed on top of the box. Movement was monitored for 2 minutes and data recorded using Powerlab™, ADI Instruments, Australia.

Testing Regime

All animals were subjected to the following test regime encompassing both behavioural and tremor testing over a defined time period (see Table 1).

TABLE 1

Testing regime.

| Time minutes (hours) | Test |
| --- | --- |
| 0 | Weight recorded |
| 60 (1.0) | Tremor test |
| 120 (2.0) | Tremor test |
| 180 (3.0) | Tremor test |
| 195 (3.25) | Tremor test |
| 210 (3.5) | Tremor test plus novel arena |
| 225 (3.75) | Tremor test |
| 240 (4.0) | Tremor test plus parallel rod |
| 270 (4.5) | Tremor test |
| 330 (5.0) | Tremor test |
| 360 (5.5) | Tremor test |
| 390 (6.0) | Tremor test |

At the end of the test period animals were euthanized by barbiturate overdose prior to perfusion fixation with 4% paraformaldehyde for routine histopathology and immunohistochemistry and blood analysis of bromide levels (results not reported as part of this application).

Figure 2:
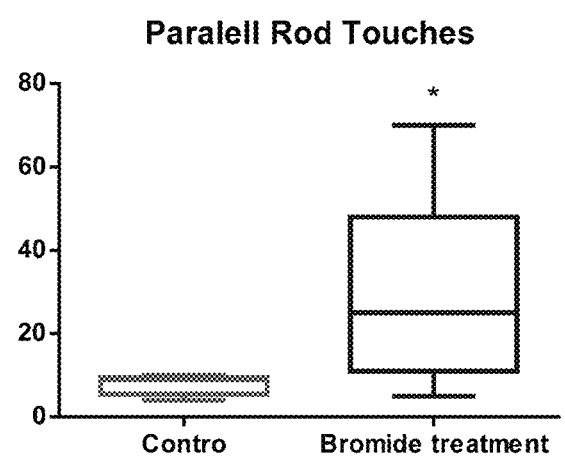
FIG. 2. Parallel Rod touches in C57/B16, 4 month old male mice given oral potassium bromide 250 mg/L (n=9) or normal drinking water (n=5) for 7 days prior to testing.
Figure 3:
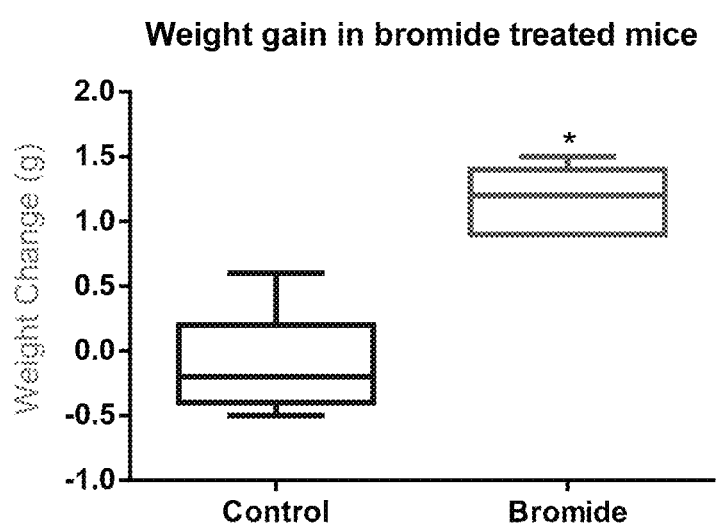
FIG. 3. Weight gain in C57/B16, 4 month old male mice given oral potassium bromide 250 mg/L (n=5) or normal drinking water (n=5) for 7 days under mildly stressful management conditions.

Results a) Novel Arena test: freezing response episodes
Number of freezing episodes while performing the novel arena test were measured as an indicator of stress. The trend was towards decreased freezing episodes in animals receiving treatment with potassium bromide (see FIG. 1).

b) Parallel rod touches
On the parallel rod test, mice had significantly more touches if they were receiving bromide treatment. Although increased touches may be exhibited with ataxia these animal show no signs of ataxia and increased touches likely represent reduced anxiety about the novel environment (see FIG. 2).

c) Weight gain
Under mild stress conditions bromide increased weight gain in age/sex matched animals as compared to control (see FIG. 3).

Conclusion

Oral potassium bromide causes significant weight gain due to decreased anxiety and subsequent appetite stimulation in animals undergoing stressful management practices.

Example 2—Determination of Pharmacokinetics of Bromide in Sheep after Single Intravenous (IV) and Oral (PO) Doses; Suitability of Bromide for Use as a Therapeutic Agent to Prevent Stress Induced Inanition in Ruminant Animals Procedure Briefly, sixteen Merino sheep were randomly assigned to two treatment groups. The intravenous (IV) group were given 120 mg/kg bromide, as sodium bromide. The per os (oral—PO group) were given 120 mg/kg bromide, as potassium bromide. Serum bromide concentrations were determined by colorimetric spectrophotometry.

Results

In summary, after IV administration the maximum concentration ($C_{max}$) was 822.11±93.61 mg/L, volume of distribution ($V_d$) was 0.286±0.031 L/kg and the clearance (Cl) was 0.836±0.255 mL/h/kg. After PO administration the $C_{max}$ was 453.86±43.37 mg/L and the time of maximum concentration ($T_{max}$) was 108±125 h. The terminal half-life (t½) of bromide after IV and PO administration was 387.93±115.35 h and 346.72±94.05 h, respectively. The oral bioavailability (F) of bromide was 92%. No adverse reactions were noted during this study in either treatment group. The concentration versus time profiles exhibited secondary peaks, suggestive of gastrointestinal cyclic redistribution of the drug.

Conclusions and Clinical Relevance

When administered PO, bromide in sheep has a long half-life (t½) of approximately 14 days, with good bioavailability.

Full Materials and Methods

Animals

Sixteen sheep, weighing between 49.5 kg and 67 kg and with an average body condition score of >2 were randomly divided into equal number (IV and PO treatment groups). Animals were placed in individual feeding pens and were fed twice daily on a ration of oats and lupins as well as ad libitum hay and water. Estimated chloride content for oats and lupins was 0.11% and 0.4% respectively.

Indwelling intravenous cannulas (Braun, Certo Splittocan 335, 16 gauge, 32 cm) were placed into the left jugular vein and secured with 2/0 polypropylene suture. A 25 cm low volume IV extension set (BMDi TUTA, 25×m minimal volume IV extension set) was connected to the catheter hub and the area was then bandaged.

Sodium bromide (NaBr) (Sigma-Aldrich) and potassium bromide (KBr) (Sigma-Aldrich) solutions were prepared using sterile water. The prepared NaBr solution was then filtered through a microfilter (0.22µ MILLEX GP, Cork, Ireland). Sodium and potassium salts were administered to dose sheep with 120 mg/kg of Br (154.6 mg/kg NaBr or 178.8 mg/kg KBr). All serum concentrations are for Br. Potassium bromide is the most readily available form of Br for oral therapy. Sodium bromide was used for the IV study because of cardiotoxicity associated with potassium. Both salts are fully disassociated in solution therefore no PK differences were expected.

IV Bromide

NaBr solution was administered through the cephalic vein using a 21 gauge needle over a period of 1 minute. Sheep were restrained in a seated position. Blood samples were collected at 0, 1, 5, 10, 15, 20 and 30 min and then at 1, 2, 3, 4, 6, 8, 10, 12, 24 h. Samples thereafter were collected at 12 h intervals to 240 h then at 24 h intervals to 336 h. A final sample was taken at 528 h. For each sample, the initial 2 mL of blood collected was discarded and a sterile syringe used to withdraw 5 mL of blood which was then placed into a plain separator blood tube (Vacuette: Greiner Bio-one). The cannulas were flushed with 3 mL of 5% heparinised saline after each collection. Each blood sample was left to stand for 30 min before centrifugation at 2000 g for 5 min. Serum was harvested and stored at −20° C. until analysis.

PO Bromide

KBr solution was administered via an orogastric tube, then flushed with 500 mL water. Blood samples were collected at 0, 1, 2, 3, 4, 6, 8, 10, 12, 24 h, then at 12 h intervals to 240 h, then at 24 h intervals to 336 h. A final sample was taken at 504 h. When collecting blood samples at 1 h through to 10 h the rumen was auscultated, over the caudo-dorsal blind sack, to determine if the high salt load affected rumen motility.

Determination of Serum Bromide Concentrations

Serum bromide concentrations were determined by colorimetric spectrophotometry as previously described (Tietz, 1976), with some modification. Briefly, 0.35 mL of serum was added to 3.15 mL of 10% trichloroacetic acid (Sigma-Aldrich) in a 10 mL centrifuge tube, vortexed, then centrifuged for 15 min at 2000 g. 2.5 mL of supernatant was then mixed with 0.25 mL of 0.5% $Au_2Cl_6$ (Sigma-Aldrich) and left to stand for 30 min. Absorbance was measured with a spectrophotometer at 440 nm. The standard curve was linear in the range of 25 μg/mL to 5000 μg/mL, $R^2$=0.9992. The lower limit of quantification was 25 μg/mL.

Pharmacokinetics

Maximum concentration ($C_{max}$) of Br and time to $C_{max}$ ($T_{max}$) were determined directly from the data. Other PK parameters were determined for each sheep by use of non-compartmental analysis with a commercial software program (Topfit 2.0, Gustav Fischer Verlag). Area under the curve ($AUC_{0-\infty}$) and area under the first moment curve ($AUMC_{0-\infty}$) were calculated by the linear trapezoidal rule (Gibalidi, 1982) the terminal elimination rate constant ($\lambda_z$) was calculated by means of log-linear regression.

Whereas parameters $C_{max}$, $T_{max}$, and AUC (where bioavailability is not absolute) are expected to differ when given IV or PO, t½ should be the same, regardless of route of administration. A t-test of the hypothesis of no difference between the t½ population means was performed. All results are expressed as mean±standard deviation (SD).

Results

All sheep in the PO group exhibited no discernable neurological effects. There was no observed alteration in rumen motility and animals continued to eat and drink. Assessment of any acute neurological effects correlating with peak Br concentration following IV administration was difficult as the sheep were held in the seated position throughout the initial 20 min, for ease of sampling. All IV sheep walked back to their individual pens and subjectively observers reported a mild tranquilising effect for approximately 1-2 h post-injection.

The relevant non-compartmental pharmacokinetic parameters derived from this study are summarised in Table 2.

TABLE 2

Pharmacokinetic parameters (mean ± SD) of bromide after intravenous and per oral administration to eight sheep at a dose of 120 mg/kg.

| Pharmacokinetic variable | Intravenous administration (mean ± SD) | Oral administration (mean ± SD) |
| --- | --- | --- |
| $C_{max}$ (mg/L) | 822.11 ± 93.61 | 453.86 ± 43.37 |
| $T_{max}$ (h) | — | 108 ± 124.86 |
| $AUC_{0-\infty}$ (mg*h/L) | 157221.8 ± 52681.53 | 143948.9 ± 26156.16 |
| $MRT_{0-\infty}$ (h) | 545.5 ± 226.1 | 413.4 ± 150 |
| Cl (mL/h/kg) | 0.836 ± 0.255 | — |
| $V_d$ (L/kg) | 0.286 ± 0.031 | — |
| $V_z$ (L/kg) | 0.393 ± 0.102 | 0.388 ± 0.037 |
| $t_{1/2}$ (h) | 387.93 ± 115.35 | 346.72 ± 94.05 |
| F | — | 0.92 |

$C_{max}$, maximum concentration; $T_{max}$, time of maximum concentration; $AUC_{0-\infty}$, area under the curve; $MRT_{0-\infty}$, mean residence time; Cl, clearance; $V_d$, volume of distribution, $V_z$, volume of distribution at pseudo-equilibrium; t½, terminal elimination half-life; F, oral bioavailability.

Figure 4:
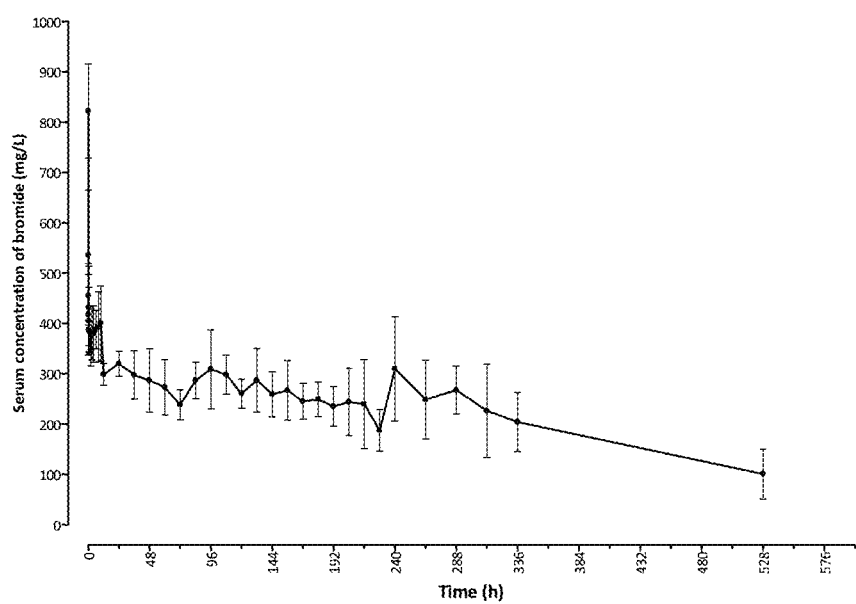
FIG. 4. Serum concentrations (mean±SD) of bromide after intravenous administration to eight sheep at a dose of 120 mg/kg.
Figure 5:
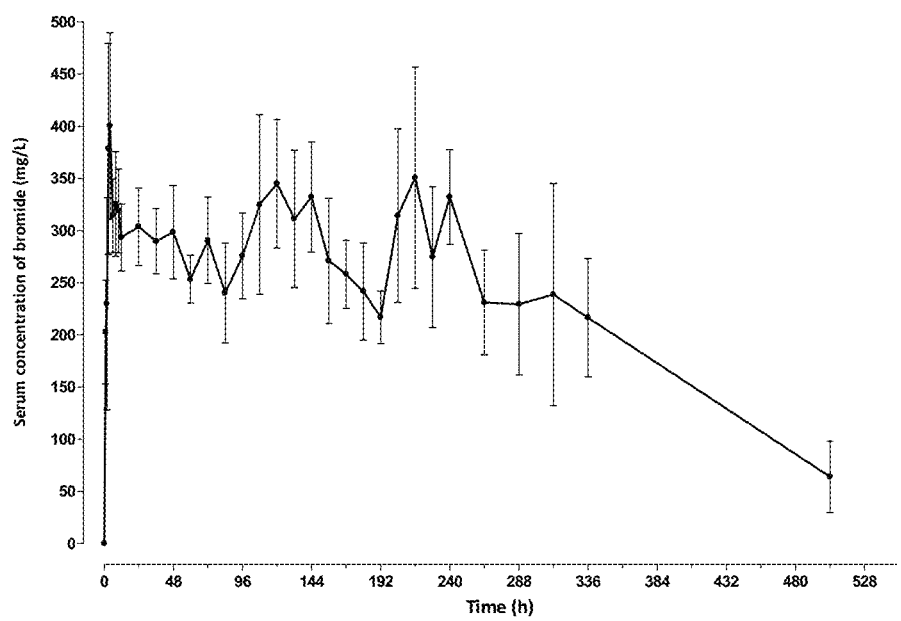
FIG. 5. Serum concentrations (mean±SD) of bromide after oral administration to eight sheep at a dose of 120 mg/kg.

The concentration-time profiles for IV and PO serum bromide are shown in FIG. 4 and FIG. 5, respectively.

The t½ of Br in sheep following PO administration was 14.4 d, the IV t½ was 16.2 d; however, the difference between groups was not statistically significant (T=0.7832, df=14, p=0.4466).

An interesting finding in this study was the numerous pronounced peaks in the PO concentration versus time curve following the initial absorption phase. These peaks approached the $C_{max}$ seen on day one, but occurred many days later (FIG. 5). Indeed, some sheep had $T_{max}$ values well beyond the initial PO absorption phase. Similar although smaller peaks were also seen with IV bromide (FIG. 4).

Study Conclusions

Bromide was absorbed rapidly following PO administration. Prior to this study, it was predicted that absorption might be delayed due to dilution, the rumen having an estimated volume of 10 L/45 kg of live weight (Hinchcliff et al., 1991). However, the $C_{max}$ in this study was similar to that measured in horses given a comparable oral Br dose (Raidal and Edwards, 2008). Ruminal epithelial cells express large conductance channels permeable to chloride (Stumpff et al., 2009) and the rumen has a high chloride absorptive capacity even against the net electrochemical gradient for the ion (Dobson and Phillipson, 1958, Scott, 1970). It is likely that these high conductance channels are also responsible for overcoming a relatively lower initial Br concentration in the ruminal/gastric fluid compared with monogastric species.

The t½ of Br in sheep, of approximately 14 d, is comparable with humans' 12 d (Harden et al., 1969) and in the dog 12-24 d (Trepanier and Babish, 1995b,a), but is considerably longer than approximately 3 d in the horse (Raidal and Edwards, 2008). This long elimination phase is a function of slow clearance; Br is not metabolised, and is subject to extensive renal tubular reabsorption, the net result being the anion is continually recycled throughout the body (Trepanier and Babish, 1995b).

In classic PO pharmacokinetic profiles of monogastric species secondary peaks are uncommon, and are usually a function of unusual drug metabolism, in particular enterohepatic recycling. Bromide, however, is not metabolised. Possible causative mechanisms are therefore limited to absorption, distribution and elimination. A Br study conducted in horses, at a similar PO dose to that used in this study produced a profile without secondary peaks in serum concentration (Raidal and Edwards, 2008).

Similar secondary peaks were also seen following IV administration, albeit much less pronounced (FIG. 4). However, it is notable that the IV peaks do appear to occur at similar time points to where they are seen following PO administration The mean bioavailability of Br in this trial was 92%, which is much higher than the estimated bioavailability 32-38% in the horse (Raidal and Edwards, 2008) and 40% in the dog (Trepanier and Babish, 1995b). This greater bioavailability in the sheep is probably due to the prolonged rumen residence time of ingestion (Cunningham et al., 2010).

The $V_d$ value of 0.286±0.031 reflects the ECF space (although volume of distribution figures are not primary measures of physiological compartments, they do often correlate well) and approximates the Va. of 0.245 L/kg used as an estimate of ECF in the sheep (Coghlan et al., 1977). The calculated volume of distribution at pseudo-equilibrium ($V_z$), when equilibration with rumen fluid is assumed, was 0.393±0.102 and 0.388±0.037 L/kg for IV and PO administration, respectively. That these measures are similar is unsurprising as $V_z$ is a proportionality factor relating to concentrations during the log-linear phase of drug elimination, from which t½ is derived.

Volume of distribution is the parameter used to calculate a loading dose (LD), using the equation $LD=V*C_{ss}$, where $C_{ss}$ is concentration steady state, or the effective concentration for a particular use (as determined by PD studies). The $V_d$ value is most appropriate where bromide is to be given as a PO bolus, and $V_z$ in circumstances where it is to be given over a few days.

Because of the long t½ following PO administration, the serum Br concentration fluctuated within a narrow range (approximately 200-400 mg/L) for 14 d. This long t½, with two fold difference between peak and trough values over a two week period confers great potential for therapeutic application, in particular prophylactic use.

The study dose of Br, 120 mg/kg, resulted in sustained Br concentrations approximating 75% of the lower bound of the anticonvulsant range (1.0-2.0 mg/ml) (Podell and Fenner, 1993). Concentrations of Br which will prevent, improve appetite or abolish inanition are unknown, although it would be assumed that in all but the most severe cases to be substantially less than those required to protect against grand mal seizures.

Several advantages of Br have now been identified by this study; Br is cheap, easy to administer, has good bioavailability and a long t½.

REFERENCES

Coghlan J A, Fan J S K, Scoggins B A, Shulkes A A (1977) Measurement of Extracellular Fluid Volume and Blood Volume in Sheep. Australian Journal of Biological Sciences 30:71-84.
Cunningham F, Elliott J, Lees P (2010) Comparative and veterinary pharmacology: Springer.
Dobson A, and Phillipson A T (1958) The absorption of chloride ions from the reticulo-rumen sac. Journal of Physiology-London 140:94-104.
Gibaldi MaP, D. (1982) Pharmacokinetics. New York: Marcel Dekker Inc
Harden R M G, Alexander W, Shimmins J, Chisholm D (1969) A comparison between the gastric and salivary concentration of iodide, pertechnetate, and bromide in man. Gut 10:928.
Hinchcliff K, Jernigan A, Upson D, Constable P (1991) Ruminant pharmacology. The Veterinary Clinics of North America Food Animal Practice 7:633.
Podell M, and Fenner W R (1993) Bromide therapy in refractory canine idiopathic epilepsy. Journal of Veterinary Internal Medicine 7:318-327.
Raidal S L, and Edwards S (2008) Pharmacokinetics of potassium bromide in adult horses. Aust Vet J 86:187-193.
Scott D (1970) Absorption of chloride from the rumen of the sheep. Res Vet Sci 11:291-293.
Stumpff F, Martens H, Bilk S, Aschenbach J, Gabel G (2009) Cultured ruminal epithelial cells express a large-conductance channel permeable to chloride, bicarbonate, and acetate. Pflugers Arch—Eur J Physiol 457:1003-1022.
Tietz N W (1976) Fundamentals of clinical chemistry.
Trepanier L A, and Babish J G (1995a) Effect of dietary chloride content on the elimination of bromide by dogs. Res Vet Sci 58:252-255.
Trepanier L A, and Babish J G (1995b) Pharmacokinetic properties of bromide in dogs after the intravenous and oral administration of single doses. Res Vet Sci 58:248-251.

Example 3—Practice of the Invention in Feedlot Integration

Steers enter the feedlot at 250 to 400 kg live-weight, heifers enter at 200 to 375 kg live-weight. The beasts spend the first two weeks is in their own pen—this period is referred to as induction. As induction is undertaken to reduce the stress of crowding and environment transition, bromide will be administered for part or the entirety of the induction phase. Provision of bromide during induction phase may occur via a single drench or injection of bromide 5 to 70% w/w or w/v, or by inclusion of bromide in feed within the range of 0.01 to 5% w/w dry matter; the lower value for a light heifer eating a bromide ration for 14 days to deliver a low dose of bromide and the upper value for a heavy steer consuming all bromide in three days to deliver a relatively high dose of bromide. Inclusion of bromide in an antibiotic, growth promotant or mineral pre-mix at 0.1 to 60% w/w is a practical method of administering bromide to a total dose of 10 to 500 mg/kg. After induction the beasts are moved into the main feedlot, where in which they remain for up to 100 days to be grown out.

Example 4—Practice of the Invention in Animal Transport

Animals are dosed with 10 to 500 mg/kg bromide either at the farm immediately prior to trucking to port, or during the induction phase at the port prior to boarding. Bromide to be administered by single injection or drench of bromide 10-70% w/w or w/v, or by inclusion of bromide in feed at a concentration of 0.01 to 5% w/w dry matter for three to five days.

Example 5—Practice of the Invention in Mulesing

Lambs are dosed with 10 to 500 mg/kg bromide, administered by single drench of bromide 5 to 70% w/w or w/v, within 48 hours of marking (including the procedures of mulesing, castration, ear tagging, vaccination and tail docking).

Example 6—Practice of Live Export of Sheep

Sheep between the ages of one and three years and weighing between 40 and 65 kg, are road transported to a registered premises. Heavier sheep, including rams up to 110 kg are also transported not uncommonly. If the premises has sheds then they stay a minimum of three days, if going onto pasture they stay a minimum of five days (excluding day of arrival and day of departure). Sheep are to be dosed with 10 to 500 mg/kg bromide either at the farm immediately prior to trucking to port, or during the induction phase at the port prior to boarding. Bromide to be administered by single injection or drench of bromide 10 to 70% w/v or w/w, or by inclusion of bromide in pellets at a concentration of 0.01 to 5% w/w dry matter for 3 to 5 days.

Example 7—Practice of Shearing Rams

Rams to be dosed with 10 to 500 mg/kg bromide, within 48 hours of shearing. Bromide to be administered by single injection or drench of bromide 20 to 70% w/v or w/w.

Example 8—Practice of Mulesing in Sheep

One of the most severe management procedures undertaken in sheep productions systems worldwide in that of mulesing. Mulesing is a routine breech modification procedure carried out in hard-bodied Merino flocks where significant amounts of skin growing in the breech region of the animal are removed to reduce the incidence of breech flystrike (invasion of tissues of the breech area by larval stages of the Australian Sheep Blowfly (*Lucilla cuprina*) later in life). Flystrike is estimated to cause losses to the Australian sheep industry of $280 million annually (2013 figures, see Australian Wool Innovation Limited 2014, and MacKinnon Project 2005) and represents one of the more adverse health states observed in sheep production systems in Australia, and is a significant ethical concern in its own right as it is a condition that will inevitably lead to a slow and painful demise if animals are left untreated. Mulesing is mainly advocated in Merino lambs which are to be retained in the flock for breeding (replacement ewe lambs or, more rarely, ram lambs) in order to limit losses from breech fly strike in the flock.

Mulesing is routinely carried out without prior analgesia or anaesthesia with only application of a spray-on local anaesthetic (e.g. Tri-Solfen, see Lomax et al, 2008) and fly repellent post tissue removal. Recovery from this procedure takes many weeks, due to the often extensive healing required for full recovery, and it is widely recognised that growth rates of mulesed lambs can be affected for many months post mulesing in production flocks. To add to this insult, mulesing is frequently carried out in combination with other management procedures including tail docking and marking (removal of testes of male lambs). The acute and chronic pain caused by a surgical procedure without anaesthetic is arguably the most extreme stressor/imposes maximal stress possible in an animal. This study is a robust test of bromide's efficacy in attenuating the negative effects of stress in ruminants.

To determine whether treatment with bromide at time of mulesing could limit the negative growth effects routinely observed in Merino flocks in response to this significant management procedure, a cohort of ewe lambs was identified which were due to undergo mulesing and tail docking as part of routine flock husbandry practices. Ewe lambs were either treated with bromide (as the potassium salt) orally immediately prior to mulesing and tail docking, or were left untreated, and their weight gain over time compared.

Methodology

A study was undertaken in a self-replacing merino flock to establish the effect of treatment with oral bromide (300 mg/kg/live weight (LW)) on weight gain post-procedure in Merino ewe lambs undergoing mulesing and tail docking as part of routine flock management practices. A total of 40 ewe lambs of approximately six weeks of age entered the trial; 20 were subjected to mulesing and tail docking but were not treated with oral bromide with 20 receiving 300 mg/kg/LW bromide orally at time of procedure.

Briefly, the lamb is placed on a mulesing cradle with the breech region presented to the operator. A sharp pair of breech shears was used to make swift incisions into the skin of the lamb, removing a tear-shaped area of skin from the breech on both sides of the tail. Each incision leaves an area of open flesh approximately 5 to 10 cm in width depending on the amount of loose skin removed. The tail of the animal is removed to the third palpable joint by incision with hot cauterising 'gas' shears and skin above the tail also pared back to expose the underlying tissue.

Animals were weighed on entry to the trial, treated orally with potassium bromide solution and then immediately subjected to mulesing and tail docking. Tri-Solfen™ (Bayer Animal Health, Gordon, NSW, Australia) was administered post-docking/mulesing to all exposed areas of underlying muscle as per manufacturer's instructions. A control cohort was subjected to the same procedures but without treatment. All lambs were then returned to the mob and allowed to mother-up before returning to their usual pasture. All lambs in the trial were weighted at 7, 14, 21, 28 and 51 days post procedure. Statistical analysis was carried out using SPSS™

Results

Figure 6:
FIG. 6. Merino ewe lamb after mulesing and tail docking procedure.

A total of 40 ewe lambs of approximately six weeks of age entered the trial. 20 animals were treated orally with 300 mg/kg LW bromide (as the potassium salt) immediately prior to mulesing and tail docking, and 20 remaining untreated whilst subjected to the same procedure. An example of an animal which has just undergone mulesing and tail docking is shown in FIG. 6.

No significant difference was observed in entry weights of treated and untreated groups to the trial (Day 0 mean live weights: Control group 13.36±0.49 kg; bromide treatment group 13.59±0.58 kg). Animals treated with oral potassium bromide (300 mg/kg LW) at time of mulesing and tail docking showed a trend towards increased weight gain compared to untreated counterparts over the duration of the trial (51 days). Mean weight gain after 51 days for each group was control 7.52±0.41 kg and bromide treatment group 8.52±0.57 kg respectively (see FIG. 7). Mean live weight on day 51 of the trial was observed to be 20.89±0.75 kg for control animals and 22.17±0.86 kg for bromide treated animals. A univariate pairwise analysis giving a significance of 0.30 (F=1.092) to this data.

Figure 7:
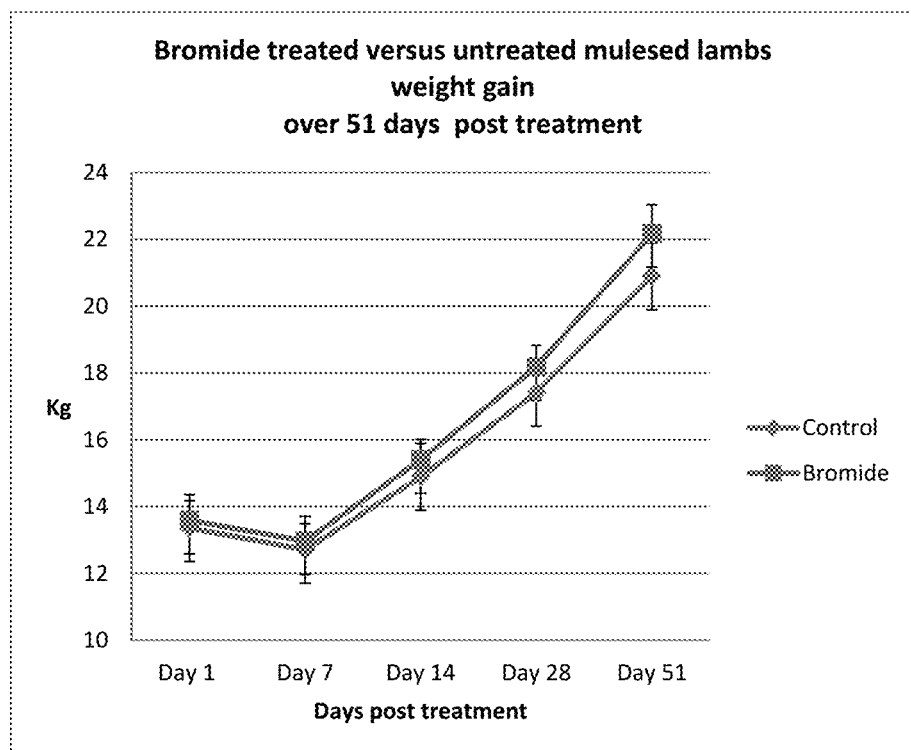
FIG. 7. Merino ewe lambs mean weight gain over time after mulesing and tail docking (bromide animals received 300 mg/kg LW oral potassium bromide immediately prior to the procedure; n=20 in both control and bromide groups).

As has been previously suggested, weight loss was observed in both groups after seven days (see FIG. 7). After 14 days, however, all animals had recovered their entry weights with bromide treated animals beginning to show enhanced weight gain compared to their untreated counterparts.

Figure 8:
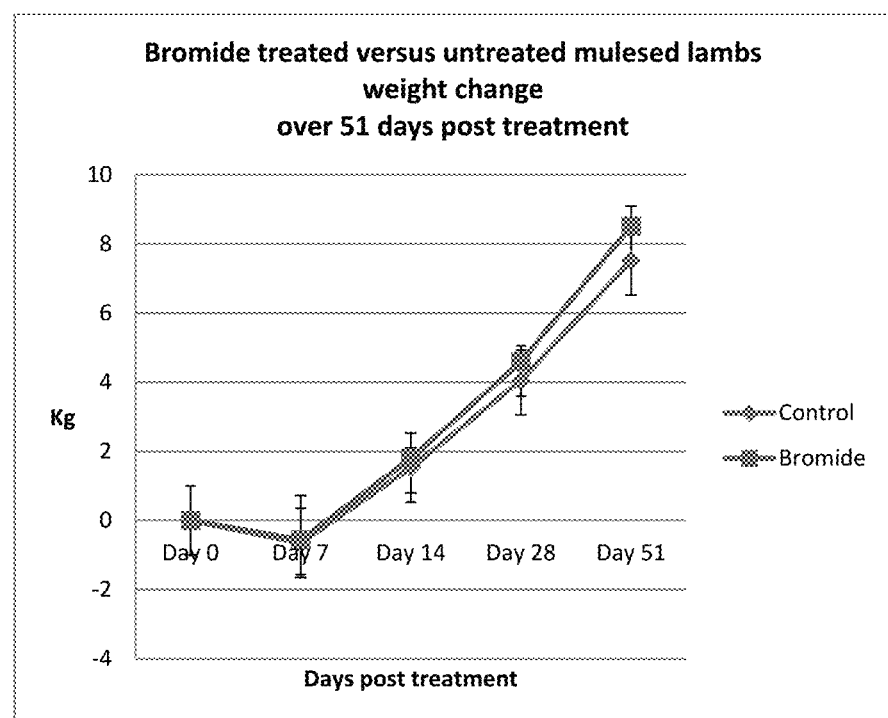
FIG. 8. Merino ewe lambs mean weight change over time after mulesing and tail docking (bromide animals received 300 mg/kg LW oral bromide, as the potassium salt, immediately prior to the procedure; n=20 in both control and bromide groups).

Live weight gain between the monitoring points (day 7, 14, 28 and 51) showed subtle differences between the treated and untreated lambs. Although both groups lost weight in the first seven days of the trial, the treated animals showed a slightly reduced weight loss compared to untreated controls (Day 1-7 mean weight change (kg): control group: −0.645±0.87 kg; bromide treatment group: −0.564±1.29 kg; see FIG. 8). Bromide treated animals also showed a marginally increased weight gain in the following 7 day period with mean weight gain for the two groups between day 7 and 14 being 1.53±0.21 kg and 1.80±0.30 kg respectively.

Figure 9:
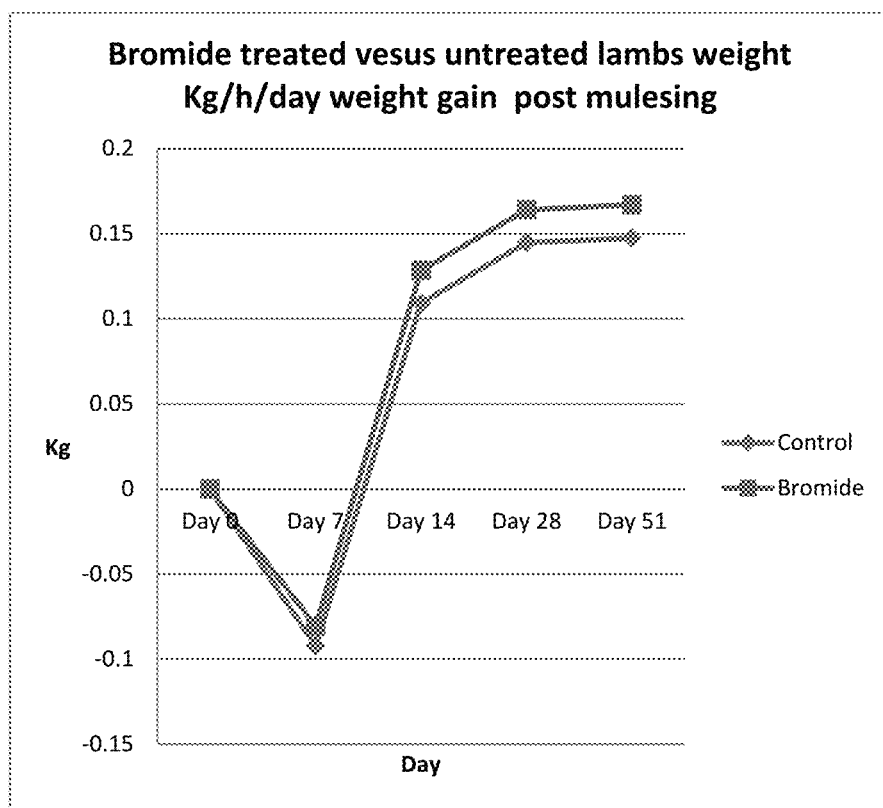
FIG. 9. Merino ewe lambs mean weight gain per head/day after mulesing and tail docking (n=20 in both control and bromide groups).

Finally, mean weight gain/head/day over the 51 days of the trial was considered (see FIG. 9). Similar to previous data, bromide treated animals showed a consistent improvement in weight gain over the duration of the trial equating to a weight gain per head per day of 0.57.

Overall, improvement in weight gain in bromide treated animals equated to a 11% increase in production gain over the duration of the trial (51 days–control group live weight gain=0.14 kg per head per day; bromide treatment group=0.16 kg per head per day).

These data equate to a measureable improvement in live weight gain after mulesing and tail docking in live weight gain in ewe lambs, particularly in the Merino breed. Early weight gain will equate to a final difference in adult weight over the same time period if animals are on the same plane of nutrition equating to a higher body condition score at time of joining which can directly translate into improved production outcomes overall.

REFERENCES

Managing breech flystrike. (2014). Australian Wool Innovation Limited. Sydney, Australia.
Report on likely increased prevalence of breech strike and increased mortalities from flystrike if sheep were not mulesed. (2005) MacKinnon Project. University of Melbourne.
Lomax, S., Sheil, M., Windsor, P. A. Impact of topical anaesthesia on pain alleviation and wound healing in lambs after mulesing. (2008). Australian Veterinary Journal. 86:5 159-168.

It will be understood that the invention disclosed and defined in this specification extends to all alternative combinations of two or more of the individual features mentioned or evident from the text or drawings. All of these different combinations constitute various alternative aspects of the invention.

What is claimed is:

1. A method for the preparation of an animal prior to subjecting the animal to a marketing or management practice, thereby preventing the induction of stress-related inanition or anxiety-related inanition in the animal during, or at completion of, the marketing or management practice,
the method including the step of administering a formulation including bromide to an animal selected for the marketing or management practice prior to subjecting the animal to a management or marketing practice in an amount effective for preventing the animal from reducing feed intake, wherein the animal does not have stress-related inanition or anxiety-related inanition at the time of administration of the formulation,
the method further including the step of providing an appetite stimulant to the animal prior to, during or after the completion of the marketing or management practice.

2. The method of claim 1, wherein the animal is a ruminant animal.

3. The method of claim 2, wherein the ruminant animal is ovine or bovine.

4. The method of claim 1, wherein the marketing or management practice is a husbandry practice selected from the group consisting of mulesing, castration, tail docking, marking, dehorning, animal transport and introduction of the animal into a feedlot.

5. The method of claim 1, wherein the formulation provides bromide in an amount of about 10 to about 750 mg/kg animal weight.

6. The method of claim 1, wherein the formulation is provided once prior to subjecting the animal to a marketing or management practice.

7. The method of claim 1, wherein the formulation is provided daily for a period of about four weeks prior to subjecting the animal to a marketing or management practice.

8. The method of claim 1, wherein the formulation is provided orally.

9. The method of claim 8, wherein the formulation is provided in the form of a drench.

10. The method of claim 8, wherein the formulation includes magnesium bromide or potassium bromide at a concentration of about 5 to about 70% w/w.

11. The method of claim 1, wherein the feed intake of the animal or the growth performance of the animal up to the time of administration of the formulation has been normal.

12. The method of claim 1, wherein the animal does not suffer grass toxicosis at the time of administration of the formulation.

13. The method of claim 1, wherein the animal does not have a movement disorder at the time of administration of the formulation.

14. The method of claim 1, wherein the animal retains a normal feed intake or growth performance subsequent to the marketing or management practice.

15. The method of claim 8, wherein the bromide is in the form of magnesium bromide or potassium bromide.

16. The method of claim 1, wherein the formulation is administered intravenously.

17. The method of claim 16, wherein the bromide is in the form of sodium bromide.

* * * * *